United States Patent [19]

Chang

[11] Patent Number: 4,748,267

[45] Date of Patent: May 31, 1988

[54] FLUOROCHEMICAL BIURET COMPOUNDS AND FIBROUS SUBSTRATES TREATED THEREWITH

[75] Inventor: John C. Chang, St. Paul, Minn.

[73] Assignee: Minnesota Mining and Manufacturing Company, St. Paul, Minn.

[21] Appl. No.: 16,138

[22] Filed: Feb. 18, 1987

Related U.S. Application Data

[62] Division of Ser. No. 595,901, Apr. 2, 1984, Pat. No. 4,668,406.

[51] Int. Cl.$^4$ .................. D02G 3/00; D06M 1/00
[52] U.S. Cl. ..................... 560/158; 252/8.75; 252/8.8; 427/393.4; 428/289; 528/70
[58] Field of Search .......... 560/158; 528/70; 252/8.75, 8.8; 428/289; 427/393.4

[56] References Cited

U.S. PATENT DOCUMENTS

| | | | |
|---|---|---|---|
| 3,329,661 | 7/1967 | Smith et al. | 260/79.3 |
| 3,398,182 | 8/1968 | Guenthner | 260/455 |
| 3,458,571 | 7/1969 | Tokoli | 260/556 |
| 3,462,296 | 8/1969 | Raynolds et al. | 117/161 |
| 3,574,791 | 4/1971 | Sherman | 260/884 |
| 3,728,151 | 4/1973 | Sherman | 117/138.8 |
| 3,896,251 | 7/1975 | Landucci | 428/290 |
| 3,916,053 | 10/1975 | Sherman et al. | 428/96 |
| 4,013,627 | 3/1977 | Temple | 526/245 |
| 4,024,178 | 5/1977 | Landucci | 260/472 |
| 4,029,585 | 6/1977 | Dettre et al. | 252/8.6 |
| 4,144,367 | 3/1979 | Landucci | 428/96 |
| 4,165,338 | 8/1979 | Katsushima et al. | 260/584 |
| 4,190,545 | 2/1980 | Marshall et al. | 252/8.75 |
| 4,215,205 | 7/1980 | Landucci | 525/331 |
| 4,264,484 | 4/1981 | Patel | 260/29.6 |
| 4,293,713 | 10/1981 | Fujimura et al. | 564/38 |
| 4,325,857 | 4/1982 | Champaneria et al. | 523/412 |
| 4,401,780 | 8/1983 | Steel | 524/225 |
| 4,426,476 | 1/1984 | Chang | 524/288 |
| 4,477,643 | 10/1984 | Keller | 252/8.75 |
| 4,504,401 | 3/1985 | Matsuo et al. | 528/70 |

FOREIGN PATENT DOCUMENTS 0103752 3/1984 European Pat. Off.

OTHER PUBLICATIONS

Banks, R. E., Ed. "Organofluorine Chemicals and Their Industrial Applications," Ellis Horwood, Ltd., West Sussex 226–230 (1979).

*Primary Examiner*—Lorraine T. Kendell
*Attorney, Agent, or Firm*—D. M. Sell; J. A. Smith; C. Truesdale

[57] ABSTRACT

Fluorochemical biurets containing one or more monovalent fluoroaliphatic radicals having at least three fully fluorinated terminal carbon atoms and one or more biuret moieties, the radicals and moieties bonded together by hetero atom-containing or organic linking groups are provided. These fluorochemical biurets are useful in the form of aqueous dispersions or emulsions or organic solutions in the treatment of fibrous substrates, such as textile fibers, to impart oil and water repellency.

15 Claims, No Drawings

FLUOROCHEMICAL BIURET COMPOUNDS AND FIBROUS SUBSTRATES TREATED THEREWITH

TECHNICAL FIELD

This application is a division of application Ser. No. 595,901, filed Apr. 2, 1984 now U.S. Pat. No. 4,668,406.

This invention relates to the treatment of fibrous substrates, such as textile fibers, carpet, paper, and leather, with fluorochemicals to impart oil and water repellency, and to the resulting treated substrates. In another aspect, it relates to the treatment of carpet fiber with a finish comprising fluorochemicals to impart oil and water repellency and soil resistance to such fiber. In another aspect, it relates to fluoroaliphatic radical-containing compositions, solutions, dispersions, and emulsions, and their preparation, which are useful in such treatment.

BACKGROUND ART

In the industrial production of textile articles, such as carpet and apparel, and such other fibrous substrates as paper and leather, it is common to treat such substrates with fluorochemicals containing fluoroaliphatic radicals (often designated by the symbol "$R_f$") to impart oil and water repellency to the surface of such substrates. Fluorochemicals of this type and their application to fibrous substrates are described in various prior art publications, e.g., U.S. Pat. Nos. 3,329,661 (Smith et al), 3,398,182 (Guenthner et al), 3,458,571 (Tokoli), 3,574,791 (Sherman et al), 3,728,151 (Sherman et al), 3,916,053 (Sherman et al), 4,144,367 (Landucci), 3,896,251 (Landucci), 4,024,178 (Landucci), 4,165,338 (Katsushima et al), 4,190,545 (Marshall), 4,215,205 (Landucci), 4,013,627 (Temple), 4,264,484 (Patel), 4,426,476 (Chang), 4,029,585 (Dettre), 3,462,296 (Raynolds et al), 4,401,780 (Steel), 4,325,857 (Champaneria et al), and Banks, R. E., Ed. "Organofluorine Chemicals and their Industrial Applications", Ellis Horwood, Ltd., West Sussex, England 226–230 (1979).

Although some fluorochemicals are useful in many applications and many are commercial products, some are relatively expensive to prepare and apply, others are difficult to apply, and others are not durable or do not impart the required properties to the extent desired.

Conventionally, fluorochemical compositions are applied to fibrous substrates, e.g., textiles and textile fiber, as solutions in organic solvents or as aqueous emulsions, as described in the above cited references, e.g., U.S. Pat. Nos. 3,329,661 and 4,024,178.

It is an object of this invention to provide a fluorochemical biuret and method for its preparation.

Another object of this invention is to provide fluorochemical biurets, including anionic and cationic derivatives thereof, useful for treating porous substrates, such as carpet fibers and carpet, for imparting oil, water and stain resistance thereto.

A further object of this invention is to provide fluorochemical biurets in the form of stable emulsions, microemulsions and dispersions useful for the treatment of porous substrates, such as fibers, paper, leather and the like to impart oil, water and stain resistance thereto.

A still further object of this invention is to provide blends of fluorochemical biurets and fluorochemical poly(oxyalkylenes), which blends can be used in the form of aqueous dispersions, emulsions and microemulsions to treat fibrous substrates such as textile fibers, filaments, yarns, or finished fibrous articles, such as carpet, and other fibrous substrates such as paper and leather, to impart oil and water repellency and stain resistance thereto.

BRIEF DESCRIPTION

This invention provides, in one aspect, fluorochemical biurets which have one or more monovalent fluoroaliphatic radicals ($R_f$), one or more biuret moieties

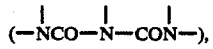

and can contain organo amino or acid moieties, such as carboxylic, sulfonic and phosphorus acid moieties, and salts formed from the compounds containing the organo amino or acid moieties, such radicals and moieties being bonded together by hetero atom-containing or organic linking groups.

This invention also provides, in another aspect, blends of (a) the fluorochemical biuret, and (b) normally liquid or low melting solid, water soluble or dispersible, fluoroaliphatic radical-containing poly(oxyalkylenes).

The fluorochemical biuret and the blends of (a) the fluorochemical biuret and (b) the fluorochemical poly(oxyalkylene) are useful in the form of aqueous suspensions, emulsions, and microemulsions, and organic solutions in the treatment of fibrous substrates, such as textile fibers during manufacture, and useful also in the treatment of finished or fabricated fibrous substrates such as carpets, paper and leather, to impart oil and water repellency thereto.

DETAILED DESCRIPTION

A class of the fluorochemical biurets of this invention can be represented by the general formula I $$R^1-NR^1CO-N(R^1)-CONR^1-R^1 \quad \text{I}$$

where each $R^1$ is the same or different and is selected from hydrogen and terminal monovalent organic radicals such as alkyl, cycloalkyl, aryl, and combinations thereof, e.g. aralkyl, and can contain fluoroaliphatic radicals ($R_f$), for example from 1 to 20 $R_f$ radicals, additional biuret moieties, for example, from 1 to 20 biuret moieties, and one or more hetero moieties, e.g. —O—, —S—,

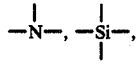

and —CO—, and is preferably free of active hydrogen atoms (i.e., hydrogen atoms of groups such as mercapto, amino, carboxyl, and aliphatic hydroxyl groups) that can readily react with isocyanate under urethane bond-forming conditions, e.g., 20° to 100° C., with the proviso that at least one $R^1$ contains $R_f$, said $R^1$ can also contain amino or acid groups. Said class also includes salts of the biurets containing the amino or acid groups.

A subclass of the fluorochemical biurets of formula I is represented by the general formula II

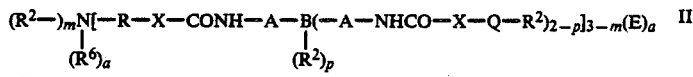

where: B is a biuret moiety,

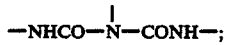

A is a divalent organic linking group linking group which can contain an $R_f$ group or additional biuret moieties; X is O, S or $NR^3$, where $R^3$ is H or lower alkyl having 1 to 4 carbon atoms; Q is a divalent linking group; $R^2$ is selected from hydrogen, and terminal monovalent organic radicals such as alkyl, cycloalkyl, aryl and combinations thereof, e.g. aralkyl, which radicals can contain fluoroaliphatic radicals ($R_f$), additional biuret moieties, and hetero moieties, e.g. —O—, —S—,

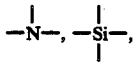

and —CO—, and is preferably free of active hydrogen atoms and may contain additional biuret moieties, each $R^2$ or A being the same or different, with the proviso that there is at least one $R^2$ or A containing at least one $R_f$, p is zero or 1, $R^6$ is selected from hydrogen, lower alkyl groups having 1 to 4 carbon atoms, and aralkyl groups having 7 to 13 carbon atoms, E is an anion derived from a protonic acid or an alkylating agent selected from alkyl chloride, alkyl bromide, alkyl iodide, dimethyl sulfate, diethyl sulfate, formic acid, acetic acid, glycolic acid, and citric acid, a is zero or 1, and m is zero, 1 or 2.

Another subclass of the fluorochemical biurets of formula I is represented by formula III

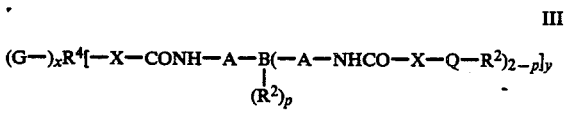

where A, B, X, Q, $R^2$, and p are the same as in formula II; $R^4$ is a monovalent or polyvalent organic linking group, preferably alkylene, G is an anionic terminal group selected from $COOM_{1/v}$, $SO_3M_{1/v}$, $PO(OM_{1/v})_2$, $OSO_3M_{1/v}$, and $OPO(OM_{1/v})_2$, where M is hydrogen or a cationic moiety, such as an alkali metal or an alkali earth metal, e.g., Na, K, and Mg, and amino salt groups, e.g., $N(C_2H_5)_3H$, $(CH_3)_2NHC_2H_4NH(CH_3)_2$,

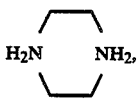

and v is the valence M, x is zero or 1, and y is 1 to 4, with the proviso that x+y is 1 to 4.

A further subclass of the fluorochemical biurets is represented by formula IV

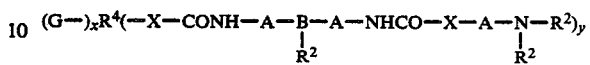

where A, B, X, $R^2$, $R_4$, G, x and y are the same as in formulas II and III.

In each of the above fluorochemicals, where there are a plurality of $R_f$, Q, A, $R^1$, $R^2$, $R_3$, $R_4$ and X groups or moieties, each can be the same or different. Also, the biurets of formulas I-IV represent individual compounds or represent mixtures of such compounds, for example, as they are obtained as products from reactions used in their preparation. In addition, small amounts of by-products, with and without the fluoroaliphatic group $R_f$, and not represented by any of the formulas I-IV, can also be present in small amounts in said mixtures or reaction products because of the reaction conditions involved in their preparation. Such presence of such small amounts of by-products, generally less than 10 weight percent, does not affect the usefulness of the fluorochemical biuret mixtures or products of this invention.

The fluoroaliphatic radical, $R_f$, referred to above, is a fluorinated, stable, inert, non-polar, preferably saturated, monovalent moiety which is both oleophobic and hydrophobic. It can be straight chain, branched chain, or, if sufficiently large, cyclic, or combinations thereof, such as alkylcycloaliphatic radicals. The skeletal chain in the fluoroaliphatic radical can include catenary oxygen, hexavalent sulfur, and/or trivalent nitrogen hetero atoms bonded only to carbon atoms, such hetero atoms providing stable linkages between fluorocarbon portions of $R_f$ and not interfering with the inert character of the $R_f$ radical. While $R_f$ can have a large number of carbon atoms, compounds where $R_f$ is not more than 20 carbon atoms will be adequate and preferred since large radicals usually represent a less efficient utilization of fluorine than is possible with smaller $R_f$ radicals. Generally $R_f$ will have 3 to 20 carbon atoms, preferably 6 to about 12, and will contain 40 to 78 weight percent, preferably 50 to 78 weight percent, fluorine. The terminal portion of the $R_f$ group has at least three fully fluorinated carbon atoms, e.g., $CF_3CF_2CF_2$— and the preferred compounds are those in which the $R_f$ group is fully or substantially completely fluorinated, as in the case where $R_f$ is perfluoroalkyl, $C_nF_{2n+1}$.

The function of the linking group Q in the above formulas is to bond the $R^2$ group, as in formulas II and III, directly to A and X groups or indirectly to A and X groups through hetero atom-containing moieties. Each Q can comprise a hetero atom-containing group or an organic group or a combination of such groups, examples of which are polyvalent aliphatic, e.g., —$CH_2$—, —$CH_2CH_2$—, and —$CH_2CH(CH_2$—$)_2$, polyvalent aromatic, oxy, thio, carbonyl, sulfone, sulfoxy, —N(CH$_3$)—, sulfonamido, carbonamido, sulfonamidoalkylene, carbonamidoalkylene, carbonyloxy, urethane, e.g., —$CH_2CH_2OCONH$—, and urylene, e.g., —NHCONH—. The linkage Q for a specific fluorochemical biuret useful in this invention will be dictated by the ease of preparation of such a compound and the availability of necessary precursors thereof. However, the Q group is preferably free of active (or isocyanate-reactive) hydrogen atoms, i.e., hydrogen atoms of groups such as mercapto, amino, carboxyl, and aliphatic hydroxyl groups that can react readily with isocyanate groups under urethane bond-forming conditions, e.g., 20°-100° C.

The divalent organic linking group A in formulas II, III, and IV above illustratively are alkylene groups, such as ethylene, isobutylene, hexylene, and methylenedicyclohexylene, having 2 to about 20 carbon atoms, aralkylene groups, such as —$CH_2C_6H_4CH_2$— and —$C_6H_4CH_2C_6H_4$—, having up to 20 carbon atoms, arylene groups, such as tolylene and various combinations of these groups. Such groups can also include from 1 to 10 $R_f$; from 1 to 10 biuret moieties and other hetero atom containing moieties, including —O—, —S—, and

e.g., —$(C_2H_4O)_2C_2H_4$—, where z is 1 to about 5. However, A is preferably free of groups with active hydrogen atoms.

The A group can be a residue of an organic diisocyanate from which the biuret, urethane, urylene and other isocyanate-derived moieties arise, that is, A can be the divalent radical obtained by removal of the isocyanate groups from an organic diisocyanate. Suitable diisocyanate precursors may be simple, e.g., hexamethylene diisocyanate, xylylene diisocyanate, tolylene-2,4-diisocyanate, methylene bis(4-phenyleneisocyanate), and mixtures thereof, or complex, as formed by the reaction of a simple diisocyanate with an organic diol or polyol in appropriate proportions to yield an isocyanate-terminated polyurethane. Other isocyanates can also be used as starting materials. Some of these are described, for example, in U.S. Patent No. 4,174,433. Representative A groups include —$CH_2C_6H_4CH_2$—$C_6H_4CH_2$—, —$C_6H_{10}CH_2C_6H_{10}$—, —$(CH_2)_6$—, —$C_6H_4CH_2C_6H_4$—, $C_8F_{17}SO_2N$-$[C_2H_4OCONHC_6H_3(CH_3)]_2$—, $C_8F_{17}SO_2N(C_2H_5)C_2H_4OCONHC_6H_{12}N(CONHC_6H_{12})_{\frac{1}{2}}$, and —$(CH_2)_6[NHCOO(CH_2)_4OCONH(CH_2)_6]_{\frac{1}{2}}$-$_{12-2}$—, and —$(CH_2)_6[NHCOO(CH_2)_4OCONH(CH_2)_6C_2]$.

Generally, the fluorochemical biurets of this invention will contain about 20 to 70 weight percent, preferably about 25 to 50 weight percent, of carbon-bonded fluorine. If the fluorine content is less than about 20 weight percent, impractically large amount of the fluorochemical biuret compounds will generally be required, while fluorine contents greater than about 70 weight percent are unnecessary to achieve the desired surface properties and thus represent an uneconomical use of fluorine.

The fluorochemical biurets of this invention can be derived from fluorine-free isocyanate-functional biurets, the latter reagents being conveniently prepared by the reaction of a diisocyanate with water as described in U.S. Pat. No. 3,124,605. A commercial biuret triisocyanate product, "Desmodur" N-100, has the principle structure

In preparing the fluorochemical biuret of this invention, a isocyanate-functional biuret, e.g., "Desmodur" N 100, can be reacted with a $R_f$-containing reagent, e.g., those containing isocyanate-reactive hydroxyl, mercapto, or amino groups. Coreactants selected from fluorine-free, isocyanate-reactive hydroxyl, mercapto and amino compounds can also be used.

Representative reaction schemes for the preparation of fluorochemical biurets of this invention are outlined below. In these schemes, a portion of the $R_f$—Q—X—H reactant can be replaced by R—Q—X—H where R is an organic radical as defined for $R^1$, preferably an alkyl radical.

SCHEME 1

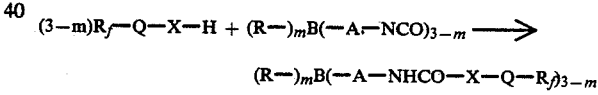

SCHEME 2

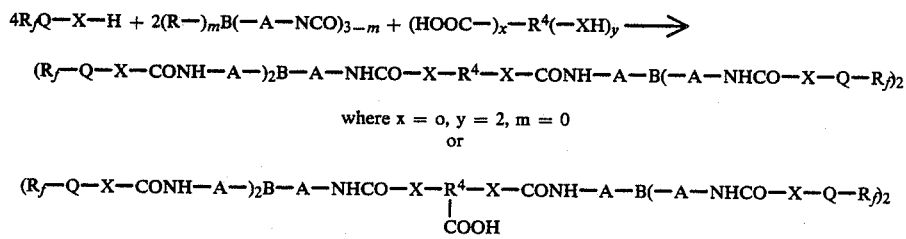

The product of Scheme 2 may then be reacted with an amine or other base to form a salt of the product.

SCHEME 3

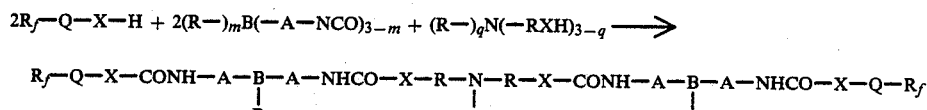

where m = 1, q = 1

The product of Scheme 3 may then be reacted with an acid or alkylating agent to form a salt of the product.

$C_8F_{17}C_2H_4SC_2H_4OH$, $(CF_3)_2CF(CF_2)_8C_2H_4OH$, $(CF_3)_2CFOC_2F_4C_2H_4OH$, $C_8F_{17}C_2H_4SO_2$

SCHEME 4

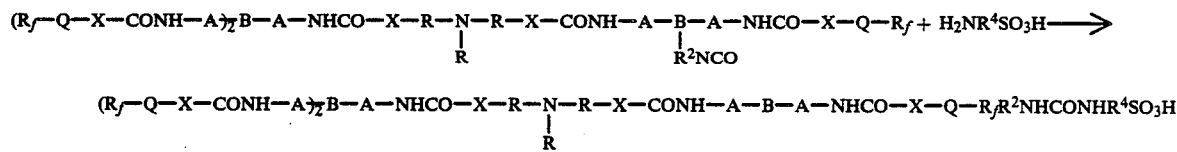

The fluorochemical biurets can also be prepared from $R_f$-containing isocyanates or amines in biuret-forming reactions. These are illustrated in the following schemes.

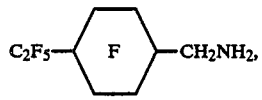

SCHEME 5

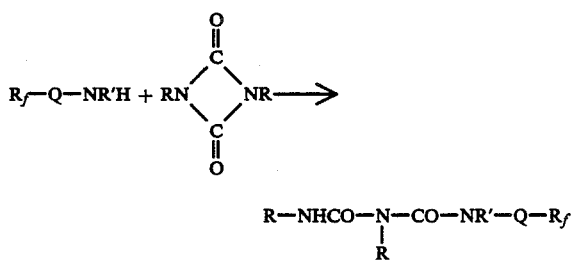

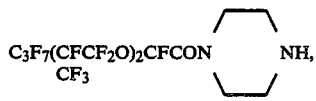

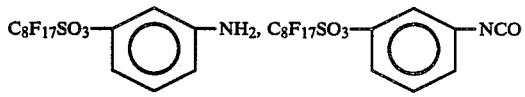

SCHEME 6

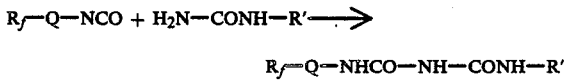

SCHEME 7

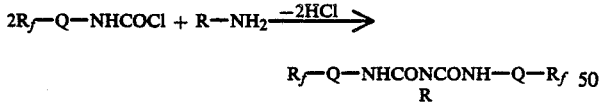

SCHEME 8

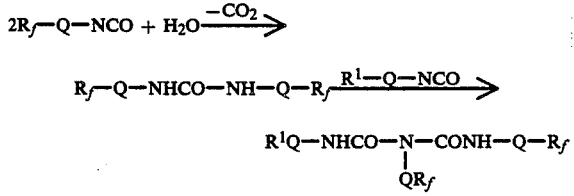

Representative $R_f$ intermediates for the preparation of the fluorochemical compositions of this invention include: $C_8F_{17}SO_2N(C_2H_5)C_2H_4OH$, $C_8F_{17}C_2H_4OH$, $C_7F_{15}CH_2OH$, $C_7F_{15}CON(C_2H_5)C_2H_4OH$, Representative organic isocyanates include tolylene-2, 4-diisocyanate, hexamethylene diisocyanate, methylenebis (4-phenyleneisocyanate), methylenebis (4-cyclohexyleneisocyanate), xylylene diisocyanate, 1-methoxy-2, 4-phenylene diisocyanate, p-(1-isocyanatoethyl)phenyl isocyanate, phenyl isocyanate, m-tolyl isocyanate, 2,5-dichlorophenyl isocyanate, hexyl isocyanate, and isophorone diisocyanate, and mixtures thereof.

Representative isocyanate-reactive alcohol, mercapto, and amine reagents include ethylene glycol, 1,3-propanediol, 1,4-butanediol, glycerine, 1,1,1-trimethylolpropane, 1,3-dihydroxy-2-propane, 3 3-mercapto-1,2-propanediol, 2-aminoethanol, -amino-1-propanol, 1,4-diaminobutane, 1,6-diaminohexane, N(3-aminopropyl)diethanolamine, 3-amino-1,2-propanediol, triethylenetetramine, 2-dimethylaminoethanol, 2-diethylaminoethanol, 2-diisopropylaminoethanol, N-methyldiethanolamine, triethanolamine, 1-methyl-3-pyrrolidinol, 2(2-hydroxyethyl)pyridine, N(2-hydroxyethyl)morpholine, 1,4-bis(2-hydroxypropyl)piperazine, 1,1-dimethyl-4-dimethylamino-n-butanol, N(2-hydroxyethyl)pyrrolidine, 1-methyl-3-piperidinol, N(2-hydroxyethyl)-N-methylaniline, 2-dimethylaminoethanethiol, N,N-bis(2-mercaptoethyl)methylamine, 4-diethyl-amino-1-methyl-n-butanol, 1-dimethylamino-2-propanol, 3-dimethylamino-1-propanol, 3-dimethylamino-2-hydroxy-n-propanol, N,N-dimethyl-1,3-propanediamine, N(2-amino- ethyl)-morpholine, 4(2-aminoethyl)-pryridine, and tris(2-aminoethyl)-amine, ethanol, octanol, octadecanol, hexylamine, dibutylamine, dodecylmercaptan, and mixtures thereof.

Representative hydroxy, mercapto and amino-group containing acids include 2,2-bis(hydroxymethyl)propionic acid, glycolic acid, 3-hydroxypropionic acid, glycine, 4-aminobutyric acid, mercaptoacetic acid, citric acid, malic acid, 3-aminopropane sulfonic acid, 4-hydroxybenzene sulfonic acid, 1,3-dihydroxybenzene sulfonic acid, and mixtures thereof.

Quaternizing alkylating agents and acids useful in this inventon include: methyl iodide, methyl bromide, allyl chloride, benzyl chloride, diethylsulfate, dimethylsulfate, bis(trifluoromethyl) sulfate, epichlorohydrin, hydrochloric acid, acetic acid, formic acid, and glycolic acid.

The fluoroaliphatic radical-containing poly(oxyalkylenes), called fluorochemical oxyalkylenes for brevity, used as component (b) in the fluorochemical blends of this invention are normally liquid or low melting solids. They contain one or more $R_f$ groups (as defined above), and one or more poly(oxyalkylene) moieties bonded together by hetero atom-containing or organic linking groups, or combinations of such groups.

A class of fluorochemical oxyalkylene used in this invention are fluoroaliphatic polymers (or oligomers, the term polymer hereinafter including oligomer unless otherwise indicated) represented by the general formulas:

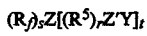   IV and

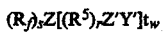   V where $R_f$ is a fluoroaliphatic radical like that described above, Z is a linkage through which $R_f$ and $(R^5)r$ moieties are covalently bonded together, $(R^5)_r$ is a poly(oxyalkylene) moiety, $R^5$ being an oxyalkylene group with 2 to 4 carbon atoms and r is an integer (where the above formulas are those of individual compounds) or a number (where the above formulas are those of mixtures) at least 5 ), generally 10 to 75 and can be as high as 100 or higher, Y is a hydrogen atom or a monovalent terminal organic radical, Y' is Y or a valence bond, with the proviso that at least one Y' is a valence bond connecting a Z-bonded $R^5$ radical to another Z, Z' is a linkage through which Y, or Y', and $R^5$ are covalently bonded together, s is an integer or number of at least 1 and can be as high as 25 or higher, t is an integer or number of at least 1, and can be as high as 60 or higher, and w is an integer or number greater than 1, and can be as high as 30 or higher.

In formulas IV and V, where there are a plurality of $R_f$ radicals, they are either the same or different. This also applies to a plurality of Z, Z', $R^5$, Y, Y', and, in formula V, a plurality of r, s, and t.

Generally, the oxyalkylene polymers will contain about 5 to 40 weight percent, preferably about 10 to 30 weight percent, of carbon-bonded fluorine. If the fluorine content is less than about 10 weight percent, impractically large amounts of the polymer will generally be required, while fluorine contents greater than about 35 weight percent result in polymers which have too low a solubility to be efficient.

In the poly(oxyalkylene) radical, $(R^5)_r$, $R^5$ is an oxyalkylene group having 2 to 4 carbon atoms, such as —OCH$_2$CH$_2$ —OCH(CH$_3$)CH(CH$_3$)—, the oxyalkylene units in said poly(oxyalkylene) being the same, as in poly(oxypropylene), or present as a mixture, as in a heteric straight or branched chain or randomly distributed oxyethylene and oxypropylene units or as in a straight or branched chain of blocks of oxyethylene units and blocks of oxypropylene units. The poly(oxyalkylene) chain can be interrupted by or include one or more catenary linkages. Where said catenary linkages have three or more valences, they provide a means for obtaining a branched chain or oxyalkylene units. The poly(oxyalkylene) radicals in the polymers can be the same or different, and they can be pendent. The molecular weight of the poly(oxyalkylene) radical can be as low as 200 but preferably is about 500 to 5,000.

The function of the linkages Z and Z' is to covalently bond the fluoroaliphatic radicals, $R_f$, the poly(oxyalkylene) moieties, $(R^5)_r$, and radicals Y and Y' together in the oligomer. Z and Z' can be a valence bond, for example where a carbon atom of a fluoroaliphatic radical is bonded or linked directly to a carbon atom of the poly(oxyalkylene) moiety. Z and Z' each can also comprise one or more linking groups such as polyvalent aliphatic and polyvalent aromatic, oxy, thio, carbonyl, sulfone, sulfoxy, phosphoxy, amine, and combinations thereof, such as oxyalkylene, iminoalkylene, iminoarylene, sulfoamido, carbonamido, sulfoamidoalkylene, carbonamidoalkylene, urethane, urea, and ester. The linkages Z and Z' for a specific oxyalkylene polymer will be dictated by the ease of preparation of such a polymer and the availability of necessary precursors thereof.

From the above description of Z and Z', it is apparent that these linkages can have a wide variety of structures, and in fact where either is a valence bond, it doesn't even exist as a structure. However large Z and Z are, the fluorine content (the locus of which is $R_f$ is in the aforementioned limits set forth in the above description, and in general the sum of Z and Z' contents of the polymer is preferably less than 10 weight percent of the polymer.

The monovalent terminal organic radical, Y, is one which is covalently bonded through Z' to the poly(oxyalkylene) radical. Though the nature of Y can vary, it preferably is such that it compliments the poly(oxyalkylene) moiety in maintaining or establishing the desired solubility of the oxyalkylene. The radical Y can be a hydrogen atom, acyl, such as $C_6H_5C(O)$—, alkyl, preferably lower alkyl, such as methyl, hydroxyethyl, hydroxypropyl, mercaptoethyl and aminoethyl, or aryl, such as phenyl, chlorophenyl, methoxyphenyl, nonylphenyl, hydroxyphenyl, and aminophenyl. Generally, $Z_Y$ will be less than 50 weight percent of the $(R^5)_r Z'Y$ moiety.

The fluoroaliphatic radical-containing poly(oxyalkylene) used in this invention can be prepared by a variety of known methods, such as by condensation, free radical, or ionic homopolymerization or copolymerization using solution, suspension, or bulk polymerization techniques, e.g., see "Preparative Methods of Polymer Chemistry", Sorenson and Campbell, 2nd ed., Interscience Publishers, (1968). Classes of representative poly(oxyalkylenes) useful in this invention include polyesters, polyurethanes, polyepoxides, polyamides, and vinyl polymers such as polyacrylates and substitute polystyrenes.

The polyacrylates are a particularly useful class of poly(oxyalkylenes) and they can be prepared, for example, by free radical initiated copolymerization of a fluoroaliphatic radical-containing acrylate with a poly(oxyalkylene) acrylate, e.g., monoacrylate or diacrylate or mixtures thereof. As an example, a fluoroaliphatic acrylate, $R_fR''$—$O_2C$—$CH=CH_2$ (where $R''$ is, for example, sulfonamidoalkylene, carbonamidoalkylene, or alkylene), e.g., $C_8F_{17}SO_2N(C_4H_9)CH_2CH_2O_2CCH=CH_2)$, can be copolymerized with a poly(oxyalkylene) monoacrylate, $CH_2=CHC(O)(R^5)_xOCH_3$, to produce a polyacrylate oxyalkylenes.

Further description of fluorochemical oxyalkylenes useful in this invention will be omitted in the interest of brevity since such compounds and their preparation are known, and are described in U.S. Pat. No. 3,787,351 and U.S. Pat. No. 4,289,892, both of which are incorporated herein by reference.

The relative amounts of component (a), the fluorochemical biurets, and component (b), the fluorochemical poly(oxyalkylene), in the fluorochemical blend used in this invention to treat porous, fibrous substrates can vary over a broad range and will be selected to provide the desired balance of surface properties on the treated fiber of the finished article. Generally, component (a) will be the major amount of the blend and component (b) will be the minor amount. The particular amount depends on the particular composition of the textile fiber or article to be treated and the particular chemical composition of (a) and (b), as well as the application procedures used.

Generally, the relative amounts of components (a) and (b) fall within the following ranges:

| Component | Amount of fluorochemical solids in blend (wt. %) | | |
|---|---|---|---|
| | General Broad Range | Preferred Broad Range | Most Preferred Range |
| (a) | 40 to 99 | 60 to 99 | 70 to 95 |
| (b) | 1 to 60 | 1 to 40 | 5 to 30 |

The fluorochemical biurets of this invention, and blends thereof with fluorochemical poly(oxyalkylenes) can be utilized as solutions in organic solvents or as aqueous emulsions or dispersions. Aqueous emulsions and microemulsions are particularly useful forms for the fluorochemical biurets and the blends thereof with poly(oxyalkylenes) of this invention because of the ease of formation and stability of these emulsions, especially when a salt forming moiety is present in the fluorochemical biuret compositions.

In the preparation of these aqueous emulsions, it is generally beneficial in ease of formation and particularly in emulsion stability to include a nonionic surfactant, thus the blends of this invention comprising (a) the fluorochemical biuret and (b) fluorochemical poly(oxyalkylenes) yield emulsions and microemulsions having excellent properties. Also these blends generally yield improved oil and water repellency when applied to porous substrates, e.g., carpet fibers and carpets.

Hydrocarbon nonionic surfactants are also beneficial in forming stable emulsions and microemulsions. These can be used in place of the fluorochemical nonionic surfactants, i.e., the fluorochemical poly(oxyalkylenes) or in addition to them as a co-surfactant. Hydrocarbon and fluorochemical anionic and cationic surfactants may also be beneficial as co-surfactants with the hydrocarbon and fluorochemical nonionic surfactants.

Representative hydrocarbon surfactants and co-surfactants useful in this invention include the following commercial poly(oxyalkylene) compounds: poly(oxyethylene) sorbitan monooleate, e.g., "Tween"80; alkylaryl polyethylene glycol ether, e.g., "Surfonic" N-120; ethoxylated lauryl alcohol, e.g., "Siponic" L-16; octylphenoxy polyethoxy ethanol, e.g., "Triton" X-102; polyethylene glycol ether of sec. alcohol, e.g., "Tergitol" 15-S-15; poly(oxyethylene) cetyl ether, e.g., "Brij" 58; octylphenoxypoly(oxyethylene) ethanol, e.g., "Igepal" CA 720, sodium lauryl sulfate, e.g. "Dupanol" QC.

Each of these surfactants and co-surfactants has a hydrophile-lipophile balance value in the range of about 12 to 18. Those hydrocarbon poly(oxyalkylenes) with higher or lower values were found not to be as useful in promoting emulsion stability and quality, but may be useful in surfactant blends.

Substrates which can be treated in accordance with this invention are textile fibers (or filaments), and finished or fabricated fibrous articles such as textiles, e.g., carpet, paper, paperboard, leather, and the like. The textiles include those made from natural fibers, such as cotton and wool and those made from synthetic organic fibers, such as nylon, polyolefin, acetate, rayon, acrylic, and polyester fibers. Especially good results are obtained on nylon and polyester fibers. The fibers or filaments as such or in an aggregated form, e.g., yarn, tow, web, or roving, or the fabricated textile, e.g., articles such as carpet and woven fabrics, can be treated with the fluorochemical biuret or blends thereof with poly(oxyalkylenes). The treatment can be carried out by applying the fluorochemical biuret composition or blends as organic solutions or aqueous or organic dispersions by known techniques customarily used in applying fluorochemicals, e.g., fluorochemical acrylate copolymers, to fibers and fibrous substrates. If desired, such known fluorochemicals as fluoroaliphatic radical-containing polymers, e.g., acrylates and methacrylates can be used in conjunction with the above-described fluorochemical biuret blends. For example, the fluorochemical treatment, with the fluorochemical being in the form of an aqueous emulsion or organic solution, can be carried out by immersing the fibrous substrates in a bath containing the cationic fluorochemical blends, padding the substrate or spraying the same with the fluorochemical emulsions or solutions, or by foam, kiss-roll, or metering applications e.g., spin finishing, and then drying the treated substrates if solvent is present. If desired, the fluorochemical composition or blends can be co-applied with conventional fiber treating agents, e.g., antistatic agents or non-aqueous fiber lubricants.

In the manufacture of synthetic organic fibers (see, for example, the review article in Kirk-Othmer, *Encyclopedia of Polymer Science and Technology*, 8, 374–404 1968), the first step that normally takes place in the process, following initial formation of the filaments (e.g., by melt spinning or solvent spinning), is coating the fiber surface with a small amount of fiber finish comprising lubricating and antistatic agents. It is particularly advantageous to treat such fibers, e.g., nylon 66 and nylon 6, with the fluorochemical biurets or blends thereof of this invention in conjunction with the spin finish being applied to such textile fibers.

Fiber finishes are generally produced in the form of dilute aqueous emulsions or as non-aqueous solutions, or dispersions, which principally contains said lubricant and antistatic agents as well as emulsifier (surfactant) and may also contain materials such as bactericides and antioxidants.

Representative lubricants include mineral oils, waxes, vegetable oils (triglycerides) such as coconut oil, peanut oil, and castor oil, synthetic oils, such as esters, polyoxyethylene derivatives of alcohols and acids, and silicone oils.

The antistatic agents, emulsifiers, and surfactants which can be incorporated into the fiber finish are selected from similar chemical classes, which include:

(a) anionics, such as fatty acid soaps, sulfated vegetable oils, salts of alkyl and ethoxylated alkyl phosphates;

(b) cationics, such as fatty amines, quaternary ammonium compounds, and quaternary phosphonium compounds;

(c) nonionics, such as glyceryl monooleate, ethoxylated alcohols, ethoxylated fatty acids, and ethoxylated fatty amides; and (d) amphoterics, such as betaines, amino acids and their salts.

A preferred method of applying the fluorochemical biuret composition blends of this invention to synthetic organic fibers is to incorporate the blend into the above-described fiber finishes in an amount sufficient to achieve the desired properties, oil and water repellency and soil resistance. Generally, the amount of fluorochemical to be used will be that sufficient to retain on the fiber of the finished article, e.g., carpet, about 200 to 1600 ppm fluorine based on the weight of the fiber. Such additions to the conventional fiber finish can be carried out without sacrificing or adversely affecting typical requirements that conventional fiber finishes must meet, namely lubrication, thermal stability, low fuming at elevated temperature, and wetting for fiber dyeability (color addition). The conventional finish components of the fiber finishes containing the fluorochemical biurets and blends thereof of this invention can be removed in a conventional manner after the fiber is manufactured in fiber form, e.g., carpets and upholstery fabrics. The fluorochemical biurets and blends thereof withstand the typical conditions encountered during fiber and yarn processing and also survive the more severe processing conditions which the greige goods encounter such as scouring and dyeing, and the finished goods encounter, such as washing, steam cleaning, and dry cleaning. The fluorochemical biurets and blends thereof do not interfere with, and are durable through, the normal fiber processing steps, e.g., drawing, texturizing, and heat setting, and provide oil and water repellency and anti-soiling properties to the finished article, e.g. carpet made from the treated fibers.

The conventional application methods used to apply finishes to fibers (or filaments) can be used with the fluorochemical biurets or blends thereof of this invention. Such methods include the use of either (a) a revolving ceramic cylinder, i.e., kiss-roll, which is partially immersed in a pan containing the fluorochemical finish, over which the moving filaments pass and pick up a thin film of finish, (b) a metering pump supplying finish through a slot or hole in a fiber guide over which the moving filaments pass, (c) an immersion finish bath, or (d) spraying devices.

Representative fluorochemical oxyalkylenes useful as component (b) in the fluorochemical blends of this invention are shown in Table 4. Generally, the preparation of the fluorochemical oxyalkylenes results in products which comprise mixtures of oxyalkylenes, the lengths of the fluoroaliphatic radical and the poly(oxyalkylene) moiety varying and the subscripts denoting the number of carbon atoms of the former and denoting the number of oxyalkylene units in a poly(oxyalkylene) segment being in both cases average numbers, and in this specification, e.g., Table 4, those subscripts should be understood as having such average values, unless otherwise indicated.

TABLE 4

1. $C_8F_{17}SO_2N(C_2H_5)CH_2CO_2(C_2H_4O)_{15}H$
2. $C_8F_{17}SO_2N(C_2H_5)C_2H_4O(C_2H_4O)_{14}H$
3. $C_8F_{17}C_2H_4O(C_2H_4O(C_2H_4O)_{15}H$
4. $C_8F_{17}SO_2N\begin{matrix}(C_2H_4O)_mH\\(C_2H_4O)_nH\end{matrix}$  (m + n = 25)
5. $C_8F_{17}SO_2N(C_2H_5)C_2H_4O(C_3H_6O)_8H$
6. $C_8F_{17}C_2H_4SCHCO_2(C_3H_6O)_mH$
   $\quad\quad\quad\quad |$
   $\quad\quad\quad CH_2CO_2(C_3H_6O)_nH$  (m + n = 20)
7. $C_8F_{17}SO_2N(C_2H_5)C_2H_4O(C_2H_4O)_{7.5}H$ Representative fluorochemical oxyalkylene polyacrylates useful as component (b) in the blends of this invention are those made by copolymerizing any of the fluorochemical acrylates of Table 5 with any of the fluorine-free poly(oxyalkylene) monomers of Table 6.

TABLE 5

1. $C_8F_{17}SO_2N(CH_3)CH_2CH_2OCOCH=CH_2$
2. $C_6F_{13}C_2H_4OCOC(CH_3)=CH_2$
3. $C_6F_{13}C_2H_4SC_2H_4OCOCH=CH_2$
4. $C_8F_{17}C_2H_4OCOC(CH_3)=CH_2$
5. $C_8F_{17}C_2H_4N(CH_3)C_2H_4OCOC(CH_3)=CH_2$
6. $C_2F_5C_6F_{10}CH_2OCOCH=CH_2$
7. $C_7F_{15}CH_2OCOCH=CH_2$
8. $C_7F_{15}CON(CH_3)C_2H_4OCOCH=CH_2$
9. $(CF_3)_2CF(CF_2)_6CH_2CH(OH)CH_2OCOCH=CH_2$
10. $(CF_3)_2CFOC_2F_4C_2H_4OCOCH=CH_2$
11. $C_8F_{17}C_2H_4SO_2N(C_3H_7)C_2H_4OCOCH=CH_2$
12. $C_7F_{15}C_2H_4CONHC_4H_8OCOCH=CH_2$
13. $C_3F_7(CFCF_2O)_2CFCH_2OCOCH=CH_2$
    $\quad\quad\quad |\quad\quad\quad\quad |$
    $\quad\quad\quad CF_3\quad\quad\quad CF_3$
14. $C_7F_{15}COOCH_2C(CH_3)_2CH_2OCOC(CH_3)=CH_2$
15. $C_8F_{17}SO_2N(C_2H_5)C_4H_8OCOCH=CH_2$
16. $(C_3F_7)_2C_6H_3SO_2N(CH_3)C_2H_4OCOCH=CH_2$
17. $C_2F_5CF\begin{matrix}CF_2CF_2\\ \diagdown \\ CF_2CF_2\end{matrix}NC_2F_4CON(CH_3)C_2H_4OCOCH=CH_2$
18. $C_6F_{13}CF=CHCH_2N(CH_3)C_2H_4OCOCH=CH_2$
19. $C_8F_{17}SO_2N(C_4H_9)C_2H_4OCOCH=CH_2$
20. $C_8F_{17}SO_2N(C_2H_5)C_2H_4OCOCH(CH_3)=CH_2$

TABLE 6

1. $CH_2=CHCO_2(C_2H_4O)_{10}(C_3H_6O)_{22}(C_2H_4O)_9C_2H_4OCOCH=CH_2$
2. $CH_2=CHCO_2(C_2H_4O)_{17}CH_3$
3. $CH_2=C(CH_3)CONH(C_3H_6O)_{44}H$
4. $CH_2=C(CH_3)CO_2(C_2H_4O)_{90}COC(CH_3)=CH_2$
5. $HS(C_2H_4O)_{23}(C_3H_6O)_{35}(C_2H_4O)_{22}C_2H_4SH$

Representative compounds of this invention were prepared from the reactants listed in Table 1, following the procedures set forth in Examples 1 and 2, with stoichiometry and structures summarized in Tables 2 and 3, respectively.

TABLE 1

| Code | Reactant formula |
|---|---|
| A1 | $C_8F_{17}SO_2N(C_2H_5)C_2H_4OH$ |
| A2 | $C_8F_{17}SO_2N(CH_3)C_2H_4OCH_2CH(CH_2Cl)OH$ |
| A3 | $C_7F_{15}C_2H_4OH$ |
| A4 | $C_8H_{17}OH$ |
| A5 | $C_2H_5C(CH_2OH)_3$ |
| B | $NCO(CH_2)_6NHCONCONH(CH_2)_6NCO$ |
|   | $\quad\quad\quad\quad\quad\quad\quad\quad\mid$ |
|   | $\quad\quad\quad\quad\quad CH_2(CH_2)_5NCO$ |
| C | $CH_3C(CH_2OH)_2COOH$ |
| D1 | $N(CH_2CH_2OH)_3$ |
| D2 | $H_2N(CH_2)_6NH_2$ |
| D3 | $N(C_2H_5)_3$ |
| E | $\underset{CH_2CHCH_2Cl}{\overset{O}{\diagup\!\!\!\diagdown}}$ |
| F | HCOOH |
| G | $(C_2H_5)_2SO_4$ |
| H | $H_2NC_3H_6SO_3H$ |

EXAMPLE 1

In a one liter, 3-neck flask fitted with a mechanical stirrer, thermometer, condenser, gas inlet tube, addition funnel and electric heating mantle was placed 164g (0.34 mole) "Desmondur" N-100 biuret triisocyanate, and 109g ethyl acetate and 4 drops stannous octoate. The mixture was heated to 82° C. and stirred under a slow $N_2$ stream while slowly adding over a period of 3 hours a solution of 319g (0.55 mole) N-ethyl (perfluorooctane) sulfonamidoethyl alcohol in 212g ethyl acetate and containing 3 drops of stannous octoate. Heating (82° C.) and stirring was continued for a period of 3 hours to yield mainly a fluorochemical biuret urethane isocyanate intermediate, $(C_8F_{17}SO_2N(C_2H_5)C_2H_4OCONHCO\text{---}_2NC_6H_{12}NCO$ or more simply ($R_f$—Q—A—$_2$B—A—NCO, and smaller amounts of B—A—Q—$R_f$)$_3$ and (OCN—A—B—A—Q—$R_f$ with B, A, Q and $R_f$ as defined above.

The temperature was lowered to 70° C. and 17.3g (0.116 mole) tris(2-hydroxyethyl) amine was added, the temperature raised to 82° C., and heating and stirring continued for an additional 1.5 hours.

Infrared absorption analysis of a small portion of reaction mixture indicated that all of the isocyanate groups had been converted to urethane groups to yield a mixture of fluorochemical biurets of composition 1 in Table 2, as the principal product.

Emulsion Preparation

The above biuret urethane solution (417g) was combined with 262g of additional ethyl acetate, 988g of distilled water, 38g "Tergitol" 15-S-40 nonionic surfactant and 5g of a fluorochemical poly(oxyalkylene), a copolymer of $C_8F_{17}SO_2N(CH_3)C_2H_4OCOCH=CH_2$, $CH_2=C(CH_3)COO(CH_2CH_2O)_{90}H$ and $CH_2=C(CH_3)COO(CH_2CH_2O)_{90}COC(CH_3)=CH_2$, and the mixture stirred and heated at 70° C. for 20 minutes, then subjected to two passes through a high shear homogenizer. The resulting emulsion was stripped of ethyl acetate (to less than 1% as measured by gas chromatography) at reduced pressure with a water aspirator and a pot temperature of up to 55° C. to yield an aqueous emulsion with 18.3% fluorochemical solids (21% total solids).

EXAMPLE 2

This example describes the preparation of an anionic biuret urethane of this invention.

Following the general procedure of Example 1, N-ethyl(perfluorooctane) sulfonamidoethyl alcohol (1269g, 2.2 moles) and "Desmondur" N-100 (653g, 1.37 moles were reacted at 82° C. in ethyl acetate solution using stannous octoate catalyst to yield mainly a fluorochemical biuret urethane isocyanate intermediate, OCN—A—B—A—Q—$R_f$)$_2$, with some B—A—Q—$R_f$)$_3$ product.

The temperature was lowered to 70° C., 30.9g (0.23 mole) 1,1,1-trimethylol propane and 46.8 g (0.35 mole) 2,2-di(hydroxymethyl) propionic acid were added, the temperature raised to 82° C. and stirring and heating continued for 3 hours. Infrared absorption analysis of a small portion of the reaction mixture indicated complete reaction of the isocyanate groups to yield the fluorochemical anionic biuret urethane composition comprising a mixture of products: b, c, d and e (structures in Table 3) in a molar ratio of about 2:1:1:1, respectively.

The triethylamine salt was prepared by adding 35.2g (0.35 mole) triethylamine to the above reaction mixture and heating at 70° C. for 2 hours to yield the biuret salt mixture of composition 2 of Table 2.

An aqueous emulsion of the above fluorochemical biuret salt product, containing 21.2% fluorochemical solids (24.3% total solids) and less than one percent ethyl acetate was prepared following the procedure of Example 1 using the same nonionic emulsifiers.

EXAMPLE 3–10

Following the general procedures of Examples 1 and 2, and using the reactants shown in Tables 1 and 2, additional fluorochemical biuret compositions and emulsions were prepared. Molar ratios of reactants are indicated in Table 2, and product compositions and structures are indicated in Tables 2 and 3.

TABLE 2

| Ex. No. | Fluorochemical biuret composition** | Reactants (moles)*** | | | | | | |
|---|---|---|---|---|---|---|---|---|
| | | Biuret | Fluorochemical alcohol | Aliphatic alcohol | Amino or hydroxy acid | Amino alcohol | Diamine | Acid, alkaline or quaternizing agent |
| 1 | a,c | B(3) | A1(6) | | | D1(1) | | |
| 2 | b,c,d,e* | B(12) | A1(24) | A5(2) | C(3) | | | D3(3) |
| 3 | a,f,k | B(5) | A1(10) | | | D1(1) | D2(1) | |
| 4 | g,c* | B(2) | A1(4) | | C(1) | | | E(1) |
| 5 | c | B(1) | A2(3) | | | | | |
| 6 | i | B(7) | A2(12) | A5(3) | | | | |
| 7 | c | B(1) | A1(3) | | | | | |
| 8 | c | B(1) | A3(3) | | | | | |
| 9 | j | B(1) | A3(2) | A4(1) | | | | |

TABLE 2-continued

| Ex. No. | Fluorochemical biuret composition** | Reactants (moles)*** | | | | | |
|---|---|---|---|---|---|---|---|
| | | Biuret | Fluorochemical alcohol | Aliphatic alcohol | Amino or hydroxy acid | Amino alcohol | Diamine | Acid, alkaline or quaternizing agent |
| 10 | i | B(3) | A1(5) | | H(1) | D1(1) | | |
| 11 | a* | B(3) | A1(6) | | | D1(1) | | F(1) |
| 12 | a* | B(3) | A1(6) | | | D1(1) | | F(0.33) |
| 13 | a* | B(3) | A1(6) | | | D1(1) | | G(1) |
| 14 | a* | B(3) | A1(6) | | | D1(1) | | G(0.33) |

*Salt or quaternized derivatives of compound of Table 3
**The fluorochemical product compositions are generally mixtures, the likely principal product(s) being shown in simplified form in Table 3, where B, A, Q and R$_f$ are as defined above.
***Reactant structure are shown in Table 1; moles shown in parenthesis are relative

TABLE 3

(a) 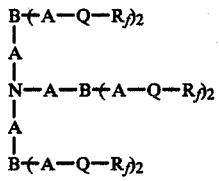

(b) 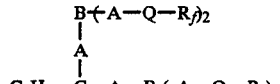

(c) B(A—Q—R$_f$)$_3$ (d) 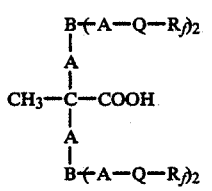

(e) 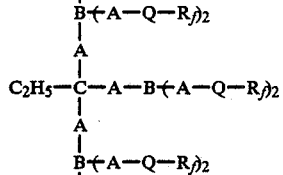

(f) 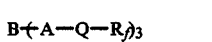

(g) 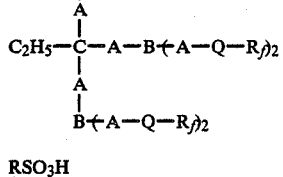

TABLE 3-continued (h) 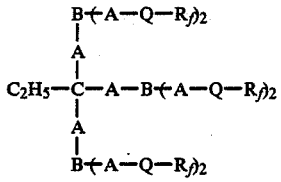

(i) 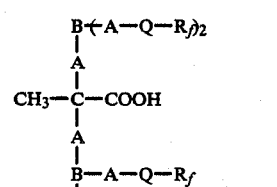

(j) R—A—B(A—Q—R$_f$)$_2$ (k) 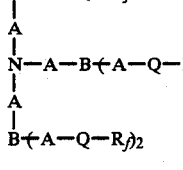

EXAMPLES 11-24

In these examples, several of the fluorochemical biurets of this invention, specified in Table 4, were used in the form of aqueous emulsions, in the presence of a nonionic textile fiber lubricant (1% SOF), and in combination with one or more nonionic surfactants, to treat samples of scoured nylon 66 greige carpet (28 oz/yd$^2$) in a padding application (71% wet pickup).

The fluorochemical treated carpet samples were placed on a paper blotter to remove excess emulsion, then dried in a circulating air oven (25 minutes at 70° C. and 5 minutes at 150° C.).

The fluorochemical treated, dried samples were then acid dyed, excess aqueous dye solution removed, samples rinsed and dried at 70° C. and then heated for 5 minutes at 130° C.

The fluorochemical treated carpet samples were analyzed for fluorine before and after dyeing to measure retention of fluorochemical on the carpet fibers. The fluorochemical treated, dyed samples were evaluated for oil repellency (OR), water repellency (WR) and walk-on soil resistance (WOS). The results are summarized in Table 4.

The water repellency test is one which is often used for this purpose. The water repellency of treated samples is measured using a water/isopropyl alcohol test, and is expressed in terms of a water repellency rating (0–10) of the treated carpet or fabric. Treated carpets which are penetrated by or resistant only to a 100 percent water/0 percent isopropyl alcohol mixture (the least penetrating of the test mixtures) are given a rating of 0, whereas treated fabrics resistant to a 0 percent water/100 percent isopropyl alcohol mixture (the most penetrating of the test mixtures) are given a rating of 10. Other intermediate values are determined by use of other water/isopropyl alcohol mixtures, in which the percentage amounts of water and isopropyl alcohol are each multiples of 10. The water repellency rating corresponds to the most penetrating mixture which does not penetrate or wet the fabric after 10 seconds contact. In general, a water repellency rating of 1 or 2, is desirable for carpet.

The oil repellency test is also one which is often used for this purpose. The oil repellency of treated carpet and textile samples is measured by AATCC Standard Test 188-1978, which test is based on the resistance of treated fabric to penetration by oils of varying surface tensions. Treated fabrics resistant only to "Nujol", a brand of mineral oil and the least penetrating of the test oils, are given a rating of 1, whereas treated fabrics resistant to heptane (the most penetrating of the test oils) are given a value of 8. Other intermediate values are determined by use of other pure oils or mixtures of oils. The rated oil repellency corresponds to the most penetrating oil (or mixture of oils) which does not penetrate or wet the fabric after 10 seconds contact rather than the 30 seconds contact of the Standard Test. Higher numbers indicate better oil repellency. In general, an oil repellency of 2 or greater is desirable for carpet.

The soil resistance of treated and untreated (control) carpet was determined by exposure to pedestrian traffic according to AATCC Test method 122-1979, the exposure site being a heavily travelled industrial area for an exposure of about 15,000 "traffics". The samples are repositioned periodically to insure uniform exposure and are vacuumed every 24 hours during the test and before visual evaluation. The evaluation employed the following "Walk-On-Soiling" (WOS) rating system:

| WOS Rating | Description |
|---|---|
| 0 | equal to control |
| ±½ | slightly better (+) or worse (−) than control |
| ±1 | impressive difference compared to control |
| ±1½ | very impressive difference compared to control |
| ±2 | extremely impressive difference compared to control |

In the tables which follow, the surfactant used is identified according to the following code:

| Code | Surfactant |
|---|---|
| A | "Tergitol" 15-S-40 |
| B | poly(oxyalkylene) copolymer of $C_8F_{17}SO_2N(CH_3)C_2H_4OCOCH=CH_2$, $CH_2=C(CH_3)COO(CH_2CH_2O)_{90}H$, and $CH_2=C(CH_3)COO(CH_2CH_2O)_{90}COC(CH_3)=CH_2$ |
| C | "Triton" X-405 |
| D | "Triton" X-102 |
| E | $C_8F_{17}SO_2N(C_2H_5)CH_2COOK$ |
| F | $C_8F_{17}SO_2NHC_3H_6N(CH_3)_3Cl$ |
| G | "Tween" 80 |
| H | "Tergitol" 15-S-30 |
| I | "Dowfax" 2A1 |

TABLE 4

| | Fluorochemical compositions | | | Properties of treated carpet | | | |
|---|---|---|---|---|---|---|---|
| | Fluorochemical | Aqueous emulsion | | Percent | | | |
| Ex. No. | Identity Table 2 No. | Surfactant Code | %* | % fluorochemical solids | fluorochemical retention through dyeing | OR | WR | WOS |
| 11 | 1 | A,B | 15,2 | 18 | 84 | 5 | 6 | +1¼ |
| 12 | 2 | A,B | 13,2 | 21 | 85 | 6 | 4 | +1½ |
| 13 | 3 | C,D | 15,3 | 17 | 100 | 5 | 7 | +1½ |
| 14 | 4 | A,E | 15,2 | 19 | 57 | 4 | 5 | +1¾ |
| 15 | 5 | A,E | 15,2 | 18 | — | 4 | 7 | +1½ |
| 16 | 6 | B | 17,5 | 19 | — | 4 | 7 | +1½ |
| 17 | 7 | H,I | 10,5 | 19 | 100 | 4 | 3 | +¾ |
| 18 | 8 | F,G | 2,13 | 16 | 69 | 6 | 8 | — |
| 19 | 9 | F,G | 2,13 | 16 | 77 | 6 | 6 | — |
| 20 | 10 | B,G | 2,13 | 17 | 73 | 5 | 6 | — |
| 21 | 11 | A,B | 15,2 | 18 | 98 | 5 | 8 | +1½ |
| 22 | 12 | B,F,G | 35,1,6 | 23 | 93 | 6 | 9 | +¾ |
| 23 | 13 | A,B | 15,2 | 18 | 94 | 5 | 8 | +1 |
| 24 | 14 | B,F,G | 35,1,6 | 22 | 76 | 5 | 8 | +1¼ |
| | Control | — | — | 0 | — | 0 | NWR** | 0 |

*Percent with respect to fluorochemical biuret
**NWR means no water-repellency

The test data show that nylon carpet pad-treated with the fluorochemical biuret has good oil and water repellency and soil resistance and that the fluorochemical biuret is retained on the carpet through the dyeing process.

EXAMPLES 25-26

Example 25 describes the treatment of nylon carpet fiber with 0.2% (baed on %F) aqueous emulsions of a fluorochemical biuret of composition No. 2 of Table 2, in combination with a 3.5 wt. % aqueous emulsion of a coconut oil-based fiber spin finish, and a fluorochemical oxyalkylene and hydrocarbon nonionic surfactant, as indicated in Table 5.

The fluorochemical spin finish emulsion composition adjusted to 0.2% fluorochemical (based on F content) was applied by a metered slot applicator to melt extruded, undrawn yarn of nylon 66. The yarn was made of 100 filaments of 20 denier (per filament). The treated yarn was continuously drawn and texturized and made into level-loop carpet (28 oz./yd$^2$), heat set at 190° C. for one minute, acid dyed, dried at 70° C. for 30 min., heated at 130° C. for 10 min., and then evaluated, together with an untreated control, Example 26, for oil and water repellency, walk-on soil resistance, and retention of fluorochemical through the dyeing process as determined by fluorine analysis. The testing results are shown in Table 5.

TABLE 5

| Ex. No. | Surfactant used with fluoro-chemical Code | % | Amount of fluorine on carpet before dyeing, ppm | after dyeing, ppm | % retention | OR | WR | WOS |
|---|---|---|---|---|---|---|---|---|
| 25 | A,B | 13,2 | 390 | 302 | 77 | 5 | 5 | +½ |
| 26 | — | — | 0 | 0 | — | 0 | | NWR |

The test data show that the fluorochemical biuret provided the carpet with good oil and water repellency and useful soil resistance and was retained on the fiber through the drawing, texturing, tufting and dyeing processes.

EXAMPLES 27-30

In examples 27 and 28, two different rainwear fabrics were treated with an aqueous emulsion of a fluorochemical biuret of composition No. 2 of Table 2, in combination with a fluorochemical oxyalkylene and hydrocarbon nonionic surfactant, as indicated in Table 6. The fabrics were treated in a padding operation, dried at 150° C. for 10 min., and evaluated, together with untreated fabrics, examples 29 and 30, for initial oil repellency (OR) and resistance to a water spray (SR), then these properties evaluated again after 5 launderings (5L) and also after one dry cleaning (DC).

The OR test used was the above-described AATCC Standard Test 118-1978, the contact time before observation being the specified 30 sec., an OR value of 3 or greater being particularly desirable for rainwear fabrics.

The water spray rating (SR) is measured by AATCC Test Method 22-1979. The spray rating is measured using a 0 to 100 scale where 100 is the highest possible rating. In general, a spray rating of 70 or greater is desirable, particularly for outerwear fabrics.

The treated fabrics were laundered using a mechanically agitated automatic washing machine capable of containing a 4 kg load, using water at 50° C. and a commercial detergent, and then the washed fabrics were tumble-dried in an automatic dryer for 40 minutes at 70° C. and pressed in a flat-bed press (at 154° C.) before testing.

The treated fabrics were dry cleaned using perchloroethylene containing 1% of a dry cleaning detergent and tumbling in a motor driven tumble jar (AATCC Test Method 70-1975) for 20 minutes at 25° C. After removing excess solvent in a wringer, samples were dried at 70° C. for 10 minutes, then pressed on each side for 15 seconds on a flat-bed press maintained at 154° C.

The test data are summarized in Table 6.

TABLE 6

| Ex. No. | Surfactant used with fluoro-chemical Code | % | % SOF$^a$ | Fab-ric$^b$ | Initial OR | Initial SR | 5L OR | 5L SR | DC OR | DC SR |
|---|---|---|---|---|---|---|---|---|---|---|
| 27 | A,B | 13,2 | 0.2 | A | 3 | 80 | 1 | 50 | 1 | 50 |
| 28 | A,B | 13,2 | 0.2 | B | 5.5 | 70 | 2 | 50 | 1 | 70 |
| 29 | — | — | 0 | A | 0 | 0 | 0 | 0 | 0 | 0 |
| 30 | — | — | 0 | B | 0 | 0 | 0 | 0 | 0 | 0 |

$^a$Percent fluorochemical solids on fabric
$^b$Fabric A is 100% woven polyester; fabric B is 100% nylon taffeta The test data show that the rainwear fabrics were provided with oil and water repellency by the fluorochemical biuret, although oil repellency decreased after laundering and dry cleaning.

EXAMPLES 31-34

In examples 31-33, water-leaf paper sheets were treated with an aqueous emulsion of a fluorochemical biuret of composition No. 2 of Table 2, in combination with a fluorochemical oxyalkylene and hydrocarbon nonionic surfactant, as indicated in Table 8.

The paper sheets were treated with various concentration of the fluorochemical emulsion compositions using a laboratory size press (yielding a 93% wet pickup) and the sheets dried in a photo sheet dryer at 150° C. and evaluated for oil and water repellancy. A comparative untreated paper sheet was also evaluated for oil and water repellancy. The results are given in Table 8.

TABLE 8

| Ex. No. | Surfactant used with fluoro-chemical Code | % | Concentration of fluorochemical in bath, wt. % | Amount of fluoro-chemical on paper, wt. % | Oil repel-lency$^a$ | Water repel-lency$^b$ |
|---|---|---|---|---|---|---|
| 31 | A,B | 13,2 | 1.54 | 0.3 | 5 | 155 |
| 32 | A,B | 13,2 | 2.56 | 0.5 | 5 | 125 |
| 33 | A,B | 13,2 | 5.12 | 1.0 | 6 | 118 |
| 34 | — | — | — | — | 0 | NWR |

$^a$This was determined by the "Kit Test" described as TAPPI Useful Method 557; the higher the value the better the repellency.
$^b$This was determined by the "Cobb Test" described as TAPPI-T441-OS-77; the lower the value, the better the water repellency.

The test results show that the paper was provided with oil and water repellency by the application of the fluorochemical biuret, with levels of repellency increasing with increased fluorochemical biuret application.

The various modifications and alterations of this invention will be apparent to those skilled in the art without departing from the scope and spirit of this invention and this invention should not be restricted to that set forth herin for illustrative purposes.

What is claimed is:

1. Fluorochemical biuret compounds each biuret compound comprising one or more monovalent fluoroaliphatic radicals having at least three fully fluorinated terminal carbon atoms and one or more biuret moieties,

said radicals bonded to the biuret moieties by hetero atom-containing or organic linking groups, which linking groups are free of active hydrogen atoms, and wherein said fluorochemical biuret compounds are represented by the general formula $$R^1-NR^1CO-N(R^1)-CONR^1-R^1$$

where each $R^1$ is the same or different, and is selected from hydrogen and terminal monovalent organic radicals, selected from alkyl, cycloalkyl, and aryl radicals and combinations thereof, with the proviso that at least one of $R^1$ is said organic radical and contains at least one fluoroaliphatic radical ($R_f$) and the proviso that at least one $R^1$ contains one or more organic radicals having at least one acid or amino moiety or is a salt formed from the compounds containing said acid or aminomoiety or that said fluorochemical biuret compound contains at least three biuret moieties.

2. Fluorochemical biuret compounds according to claim 1 wherein said biuret compounds are represented by the general formula

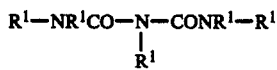

where B is a biuret moiety

$R^2$ is a terminal, monovalent organic radical selected from alkyl, cycloalkyl, and aryl radicals and combnations thereof, each $R^2$ being the same or different, A is a divalent organic linking group, X is O, S or $NR^3$, where $R^3$ is H or lower alkyl group, Q is a hetero atom-containing linking group or an organic linking group, or a combination of said groups, with the proviso that at least one of $R^2$ or A contain at least one fluoroaliphatic radical ($R_f$), $R^6$ is selected from hydrogen, lower alkyl groups having 1 to 4 carbon atoms, and aralkyl groups having 7 to 13 carbon atoms, E is an anion derived from a protonic acid or an akylating agent, a is zero or 1, p is zero or 1, and m is zero, 1 or 2.

3. Fluorochemical biurets compounds according to claim 2 wherein E is derived from a protonic acid or alkylating agent selected from alkyl chloride, alkyl bromide, alkyl iodide, dimethyl sulfate, diethyl sulfate, formic acid, acetic acid, glycolic acid, hydrochloric acid and citric acid.

4. Fluorochemical biurets compound according to claim 2 wherein $R^2$ is $C_nF_{2n+1}$ where n is 6 to 12, A is selected from $-CH_2-_6$ and $-C_6H_3(CH_3)-$, X is selected from $-O-$ or $-NH-$, Q is selected from and $-CH_2-_b$ $SO_2NR^3(CH_2)_b$ where b is 1 to 6 and $R^3$ is an alkyl group having 1 to 4 carbon atoms, and p, m, and a are zero.

5. Fluorochemical biuret compounds according to claim 2 wherein $R^2$ is $C_nF_{2n+1}$ where n is 6 to 12, A is selected from $-CH_2-_6$ and $-C_6H_3(CH_3)-$, X is selected from $-O-$ or $-NH-$, Q is selected from $-CH_2-_b$ and $SO_2NR^3(CH_2)-$ where b is 1 to 6 and $R^3$ is an alkyl group having 1 to 4 carbOn atoms, E is an anion derived from a protonic acid or an alkylating agent selected from formic acid, glycolic acid, acetic acid, diethyl sulfate, and alkyl chloride, p is zero, m is zero, and a is 1.

6. Fluorochemical biuret compounds according to claim 2 wherein $R^2$ is

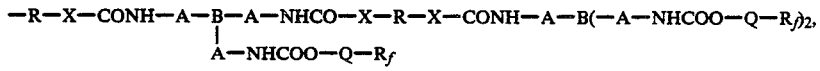

$R_f$ is $C_nF_{2n+1}$ where n is 6 to 12, A is selected from $-CH_2-_6$ and $-C_6H_3(CH_3)-$, R is $-CH_2-_b$ where b is 1 to selected from $-CH_2-_b$ and $SO_2NR^3(CH_2)-$ where b is 1 to 6, $R^3$ is lower alkyl having 1 to 6 carbon atoms, p is zero or 1, m is 1 or 2, and a is zero.

7. Fluorochemical biuret compounds, each biuret compound comprising one or more monovalent fluoroaliphatic radicals having at least three fully fluorinated terminal carbon atoms and one or more biuret moieties,

said radicals bonded to the biuret moieties by hetero atom-containing or organic linking groups, which linking groups are free of active hydrogen atoms, and wherein said biuret compounds are represented by the general formula

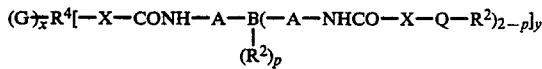

where B is a biuret moiety, $-NHCONCONH-$; $R^2$ is a terminal monovalent organic radical selected from alkyl, cycloalkyl, and aryl radicals any combinations thereof, each $R^2$ being the same or different; $R^4$ is a polyvalent organic radical; A is a divalent organic linking group with the proviso that at least one of $R^2$ or A contain at least one fluoroaliphatic radical ($R_f$); X is O, S or $NR^3$, where $R^3$ is H or a lower alkyl group; Q is a hetero atom-containing linking group or an organic linking group, or a combination of said groups; G is an anionic terminal group selected from $COOM_{1/v}$, $SO_3M_{1/v}$, $OSO_3M_{1/v}$, $PO(OM_{I/v})_2$ and $OPO(OM_{1/v})_2$ where M is hydrogen or a cationic moiety and v is the valence of M, x is 1; p is zero or 1; and y is an integer of 1 to 4, with the proviso that x+y is an integer of 2 to 4.

8. Fluorochemical biuret compounds according to claim 7 wherein G is selected from COOM and $SO_3M$ where M is selected from $NH_4$, $N(R^3)_3H$ where $R^3$ is an alkyl group having 1 to 4 carbon atoms, $N(CH_2CH_2OH)_3H$, Na and K, $R^2$ is $-A-NHCO-X-$ —R—X—CONH—A—B(—A—NHCO—X—Q—R$_f$)$_2$]$_2$, where R is selected from —CH$_2$C(C$_2$H$_5$)(—CH$_2$—)$_2$ and —CH(CH$_2$—)$_2$, R$_f$ is C$_n$F$_{2n+1}$ where n is 6 to 12, a is selected from —CH$_2$—$_6$ and —C$_6$H$_3$(CH$_3$)—, R$^4$ is —(CH$_3$)C(CH$_2$—)$_2$ when y is 2 and R$^4$ is —CH$_2$—$_b$, where b is 1 to 6, when y is 1, X is —O— or —NH—, Q is selected from —CH$_2$—$_b$ and SO$_2$NH$^3$(CH$_2$)$_b$ where b is 1 to 6 and R$^3$ is an alkyl group having 1 to 4 carbon atoms, p is zero or 1, x is 1.

9. Fluorochemical biuret, each biuret compound comprising one or more monovalent fluoroaliphatic radicals having at least three fully fluorinated terminal carbon atoms and one or more biuret moieties,

said radicals bonded to the biuret moieties by hereto atom-containing or organic linking groups, which linking groups are free of active hydrogen atoms, and wherein said biuret compounds are represented by the general formula

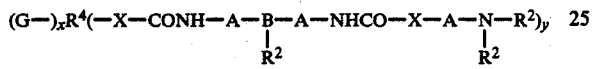

where B is a biuret moiety, —NHCONCONH—, R$^2$ is a terminal monovalent organic radical selectled from alkyl, cycloalkyl and aryl radicals and combinations thereof, each R$^2$ being the same or different, R$^4$ is a polyvalent organic radical, A is a divalent organic linking group with the proviso that at least one of R$^2$ or A contain at least one fluoroaliphatic radical, G is an anionic terminal group selected from COOM$_{1/\nu}$, SO$_3$M$_{1/\nu}$, OSO$_3$M$_{1/\nu}$, PO(OM$_{1/\nu}$)$_2$ and OPO(OM$_{1/\nu}$)$_2$ where M is hydrogen or a cationic moiety and v is the valence of M, n is 1 or 2, x is 1, and y is an integer of 1 to 4, with the proviso that x+y is an integer of 2 to 4.

10. Fluorochemical biurets compounds according to claim 9 wherein G is selected from —CO$_2$M and —SO$_3$M where M is selected from H, N(C$_2$H$_5$)$_3$H, K, and Na, R$^2$ is selected from —A—NHCO—X—Q—R$_f$ and —R—X—CONH—A-13  B[A—NHCO—X—A—B(—A—NHCO—X—Q—R$_f$)$_2$]2 where R$_f$ is C$_n$F$_{2n+1}$ where n is 6 to 12, and Q is selected from —CH$_2$—$_b$ and —SO$_2$NR$^3$(CH$_2$—$_b$ where b is 1 to 6 and R$^3$ is an alkyl group having 1 to 4 carbon atoms, A is selected from —CH$_2$—$_6$ and —C$_6$H$_3$(CH$_3$)—, R$^4$ is —CH$_2$—$_b$, where b is 1 to 6, X is —O—, —NH—, R is —CH$_2$—$_b$ where b is 1 to 6, x is 1 and y is 1.

11. Fluorochemical biurets compounds according to claim 1 or 9, or 2 or 7 wherein said terminal monovalent organic radical contains at least one biuret moiety.

12. Fluorochemical biurets compounds according to claim 1, or 9 2 or 7 wherein A contains at least one biuret moiety.

13. Fluorochemical biuret compound according to claim 1 wherein said compound is represented by the formula

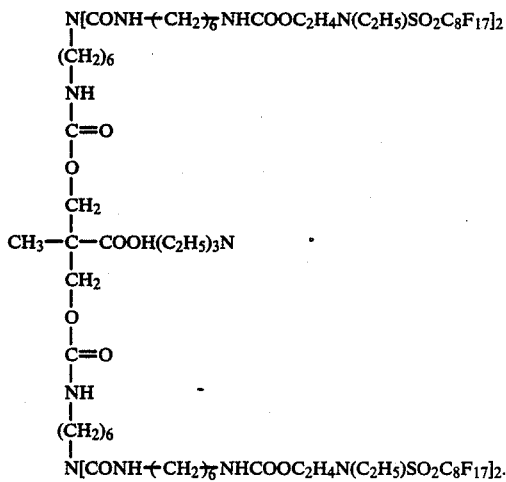

14. Fluorochemical biuret compound according to claim I wherein said compound is represented by the formula N{C$_2$H$_4$OCONH—CH$_2$—$_6$N[CONH—CH$_2$)$_6$NHCOOC$_2$H$_4$N (C$_2$H$_5$)SO$_2$C$_8$F$_{17}$]$_2$}$_3$.

15. Fluorochemical biuret compound according to claim 1 wherein said compound is represented by the formula HCOO$^\ominus$HN$^\oplus${C$_2$H$_4$OCONH—(—CH$_2$—)$_6$—N[CONH—(—CH$_2$—)$_6$—NHCOOC$_2$H$_4$N(C$_2$H$_5$)SO$_2$C$_8$F$_{17}$]$_2$}$_3$.

* * * * *

UNITED STATES PATENT AND TRADEMARK OFFICE
CERTIFICATE OF CORRECTION

PATENT NO. : 4,748,267

DATED : MAY 31, 1988

INVENTOR(S) : JOHN C. CHANG

It is certified that error appears in the above-identified patent and that said Letters Patent is hereby corrected as shown below:

Col. 23, line 29, "aminomoiety" should be --amino moiety--.

Col. 23, line 46, "combnations" should be --combinations--.

Col. 23, line 58, "biurets" should be --biuret--.

Col. 23, line 64, "biurets" should be --biuret--.

Col. 23, line 67, delete "and".

Col. 23, line 68, "$-CH_2-_b SO_2 NR^3(CH_2)_b$" should be -- $(CH_2)_b$ and $SO_2NR^3(CH_2)_b$ --.

Col. 24, line 5, "$-CH_2-_6$" should be -- $(CH_2)_6$ --.

Col. 24, line 7, "$-CH_2-_b$ and $SO_2NR^3(CH_2)-$" should be -- $(CH_2)_b$ and $SO_2NR^3(CH_2)_b-$ --.

Col. 24, line 22, "$CH_2-_6$" should be -- $(CH_2)_6$ -- and "$-CH_2-_b$" should be -- $(CH_2)_b$ --.

Col. 24, line 23, "is 1 to selected from $-CH_2-_b$ and $SO_2NR^3(CH_2)-$" should be -- is 1 to 6, Q is selected from $(CH_2)_b$ and $SO_2NR^3(CH_2)_b-$ --.

UNITED STATES PATENT AND TRADEMARK OFFICE
CERTIFICATE OF CORRECTION

PATENT NO. : 4,748,267

DATED : MAY 31, 1988

INVENTOR(S) : JOHN C. CHANG

It is certified that error appears in the above-identified patent and that said Letters Patent is hereby corrected as shown below:

Col. 25, line 3, "$-CH(CH_2-)_2$," should be -- $-CH(CH_2-)$ --.

Col. 25, line 4, "a is selected from $-CH_2-_6$" should be -- A is selected from $(CH_2)_6$ --.

Col. 25, line 6, "$-CH_2-_b$" should be -- $(CH_2)_b$ -- .

Col. 25, line 10, "Fluorochemical biuret," should be -- Fluorochemical biuret compounds, --.

Col. 25, line 44, "-R-X-CONH-A-13 B[A-NHCO-X-" should be -- -R-X-CONH-A-B[-A-NHCO-X- --.

Col. 26, line 2, "$-CH_2-_b$" should be -- $(CH_2)_b$ --.

Col. 26, line 4, "$-CH_2-_6$" should be -- $(CH_2)_6$ --.

UNITED STATES PATENT AND TRADEMARK OFFICE
CERTIFICATE OF CORRECTION

PATENT NO. : 4,748,267

DATED : MAY 31, 1988

INVENTOR(S) : JOHN C. CHANG

Page 3 of 5

It is certified that error appears in the above-identified patent and that said Letters Patent is hereby corrected as shown below:

Col. 26, line 5, "$-CH_2-_b$" should be -- $(CH_2)_b$ --.

Col. 26, line 6, "$-CH_2-_b$" should be -- $(CH_2)_b$ --.

Col. 26, line 7, "biurets" should be -- biuret --.

Col. 26, line 10, "biurets" should be -- biuret --.

Col. 26, line 38, "claim I" should be -- claim 1 --.

Col. 3, line 14, "linking group repeated twice, delete "linking group".

Col. 3, line 57, insert -- or -- after formula.

Col. 4, line 12, "$R_4$" should be -- $R^4$ --.

Col. 4, line 15, "$R_3$, $R_4$" should be -- $R^3$, $R^4$ --.

Col. 6, line 1 & 2, delete "12-2-, and $-(CH_2)_6[NHCOO(CH_2)_4-CONH(CH_2)_6C_2$."

Col. 8, line 2 & 3, insert after $SO_2$ -- $N(CH_3)C_4H_8OH$, $C_8F_{17}SO_2N(CH_3)C_3H_6NH_2$, --.

UNITED STATES PATENT AND TRADEMARK OFFICE
CERTIFICATE OF CORRECTION

PATENT NO. : 4,748,267

DATED : MAY 31, 1988

INVENTOR(S) : JOHN C. CHANG

It is certified that error appears in the above-identified patent and that said Letters Patent is hereby corrected as shown below:

Col. 8, lines 32 & 33, insert after formula -- $C_8F_{17}C_6H_4NH_2$, $C_8F_{17}C_6H_4NCO$, $C_7F_{15}CH_2NCO$, $C_8F_{17}C_2H_4SH$, and $C_7F_{15}CON(CH_3)C_2H_4SH$. --.

Col. 8, line 46, delete extra "3" after 2-propane --.

Col. 8, line 47, insert --3-- before -amino-1-.

Col. 9, line 33, "$(R^5)r$" should be -- $(R^5)_r$ --.

Col. 10, line 1, insert -- $-OCH_2CH_2CH_2-$, $-OCH(CH_3)CH_2-$, and -- after "$-OCH_2CH_2-$,".

Col. 10, line 36, "Z" should be --Z'--.

Col. 10, line 36, insert closed parenthesis after "$R_f$".

Col. 10, line 53, "Zy" should be --Z'Y--.

Col. 14, line 9, "$C_8F_{17}C_2H_4O(C_2H_4O(C_2H_4O)_{15}H$" should be -- $C_8F_{17}C_2H_4O(C_2H_4O)_{15}H$ --.

Col. 15, line 42, "$(OCN-A-B-A-Q-R_f$ should be -- $(OCN-A\!\!+\!\!_2B-A-Q-R_f$ --.

UNITED STATES PATENT AND TRADEMARK OFFICE
CERTIFICATE OF CORRECTION

PATENT NO. : 4,748,267
DATED : MAY 31, 1988
INVENTOR(S) : JOHN C. CHANG

It is certified that error appears in the above-identified patent and that said Letters Patent is hereby corrected as shown below:

Col. 16, lines 23 & 24, "OCN-A-B-A-Q-$R_f$)$_2$, with some B-A-Q-$R_f$)$_3$" should be -- OCN-A-B$($A-Q-$R_f$)$_2$, with some B$($A-Q-$R_f$)$_3$ --.

Col. 15, lines 40 & 41, "($R_f$-Q-A-$_2$B-A-NCO should be -- ($R_f$-Q-A$)_2$B-A-NCO --.

Col. 15, line 42, "B-A-Q-$R_f$)$_3$ should be -- B$($A-Q-$R_f$)$_3$ --.

Signed and Sealed this

Twenty-sixth Day of December, 1989

*Attest:*

JEFFREY M. SAMUELS

*Attesting Officer*  *Acting Commissioner of Patents and Trademarks*